(12) United States Patent
Affaitati et al.

(10) Patent No.: US 8,440,680 B2
(45) Date of Patent: May 14, 2013

(54) 2,6-DIPHENYL-4,8-DIAZOADAMANTAN-1-ONE AND DERIVATIVES THEREOF, PROCESS OF MANUFACTURE AND USE FOR THE FORMULATION OF SOLUTIONS WITH STERILIZING AND DISINFECTANT EFFECT

(75) Inventors: Pietro Affaitati, Albano Laziale (IT); Giancarlo Folchitto, Rome (IT)

(73) Assignee: Pietro Affaitati, Albano Laziale (IT)

( * ) Notice: Subject to any disclaimer, the term of this patent is extended or adjusted under 35 U.S.C. 154(b) by 603 days.

(21) Appl. No.: 12/520,821

(22) PCT Filed: Nov. 12, 2007

(86) PCT No.: PCT/IB2007/054594
§ 371 (c)(1),
(2), (4) Date: Nov. 10, 2009

(87) PCT Pub. No.: WO2008/078208
PCT Pub. Date: Jul. 3, 2008

(65) Prior Publication Data
US 2010/0069415 A1    Mar. 18, 2010

(30) Foreign Application Priority Data

Dec. 21, 2006 (IT) .............................. RM2006A0688

(51) Int. Cl.
*A61K 31/505* (2006.01)
(52) U.S. Cl.
USPC ........................................................ 514/267
(58) Field of Classification Search ........................ None
See application file for complete search history.

(56) References Cited

U.S. PATENT DOCUMENTS

2004/0022672 A1* 2/2004 Castellini ................... 422/28

FOREIGN PATENT DOCUMENTS

| EP | 1 059 292 A2 | 12/2000 |
| EP | 1 389 470 A1 | 2/2004 |
| RU | 1 246 568 A1 | 8/1995 |
| WO | 2007/007224 A1 | 1/2007 |

OTHER PUBLICATIONS

P. H. McCabe, et al, Conformational Control in the 3, 7-Diazabicycl0[3.3.1]Nonane System, Journal of the Chemical Society, Chemical Communications, 1985, p. 625-626 No. 10, Letchworth, GB.
Database Beilstein, Beilstein Institute for Organic Chemistry, Frankfurt-Main, DE; BRN 5410002 5410687 5411459; abstracting D. Misiti, et al, Gazzetta Chimica Italiana, 1966, p. 1696-1714, vol. 96, Societa Chimica Italiana, Rome, IT.
Database Beilstein, Beilstein Institute for Organic Chemistry, Frankfurt-Main, DE; Reaction ID 855934 abstracting Chiavarelli, et al, Gazzetta Chimica Italiana, 1958, p. 1234-1243, vol. 88, Societa Chimica Italiana, Rome, IT.
Database Beilstein Beilstein Institute for Organic Chemistry, Frankfurt-Main, DE; Substance ID 4603166 abstracting A. Kuznetsov, et al, Chccal; Chem. heterocycl. Compd. (Engl. Transl.); EN; 21; 12; 1985; 1382-1388; KGSSAQ; Khim. geterotsidl. Soedin.; RU; 21; 12; 1985; 1679-1685.
Database Beilstein, Beilstein Institute for Organic Chemistry, Frankfurt-Main, DE; BRN 308161, Entry date Nov. 28, 1988; Update Date Jan. 24, 1994; abstracting A. Kuznetsov, et al, Chccal; Chem. heterocycl. Compd. (Engl. Transl.); EN; 21; 12; 1985; 1382-1388; KGSSAQ; Khim. geterotsidl. Soedin.; RU; 21; 12; 1985; 1679-1685.
Database Beilstein, Beilstein Institute for Organic Chemistry, Frankfurt-Main, DE; BRN 698357; abstracting D. Misiti, et al, Gazzetta Chimica Italiana, 1970, p. 495-518, vol. 100; Societa Chimica Italiana, Rome, IT.
Database Beilstein, Beilstein Institute for Organic Chemistry, Frankfurt-Main, DE; BRN 706048; abstracting Chiavarelli, et al, J. Med. Pharm. Chem.; 5:1293-1295 (1962).
Database CA [Online] Chemical Abstracts Service, STN CA Caesar accession No. 1279; abstracting TS. E. Agadihanyan, et al, Patent No. SU1246568, "2' ,2' ,5,7-tetramethyl-6-oxospiro-(1,3-diazaadamantane-2, 4'-tetrahydrothiopyran possessing antistaphylococcic activity", issued Aug. 27, 1995.

* cited by examiner

*Primary Examiner* — Noble Jarrell
(74) *Attorney, Agent, or Firm* — Browdy and Neimark, PLLC

(57) ABSTRACT

A chemical compound having the following structural formula wherein optionally at least one of the phenyl —$C_6H_5$ groups bound to the Carbon atoms in position 2 and 6 is independently substituted with a methyl —$CH_3$ or ethyl —$C_2H_5$ group, and wherein optionally the =$CH_2$ group in position 10 is substituted with a sulphinyl =SO or sulphonyl =$SO_2$ group. Subject-matter of the invention is also a process of manufacture of 2,6-diphenyl-4,8-diazoadamantan-1-one and the use of this chemical compound and above-mentioned derivatives thereof as components for the formulation of solutions with sterilizing and disinfectant effect. The figure shows the IR spectrum of 2,6-diphenyl-4,8-diazoadamantan-1-one.

2 Claims, 1 Drawing Sheet

2,6-DIPHENYL-4,8-DIAZOADAMANTAN-1-ONE AND DERIVATIVES THEREOF, PROCESS OF MANUFACTURE AND USE FOR THE FORMULATION OF SOLUTIONS WITH STERILIZING AND DISINFECTANT EFFECT

The present invention refers to the field of solutions with disinfectant and sterilizing activity, even though its subject-matter has a significance broader than this scope.

In fact, subject-matter of the present invention is a novel molecule, and derivatives thereof with alike properties, suitable for being used for the formulation of solutions with disinfectant and sterilizing activity.

It is a chemical compound having structural formula

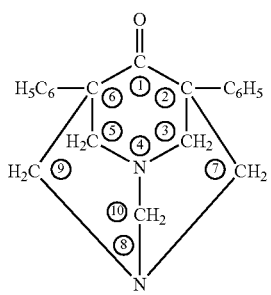

wherein optionally at least one of the phenyl —$C_6H_5$ groups bound to the Carbon atoms in position 2 and 6 may be independently substituted with a methyl —$CH_3$ or ethyl —$C_2H_5$ group, and wherein optionally the =$CH_2$ group in position 10 may be substituted with a sulphinyl =SO or sulphonyl =$SO_2$ group.

In particular, subject-matter of the invention is the chemical compound 2,6-diphenyl-4,8-diazoadamantan-1-one.

Subject-matter of the invention is also a process of manufacture of 2,6-diphenyl-4,8-diazoadamantan-1-one, wherein 1-3 moles of aromatic derivative with a dibenzyl-ketone type structure are reacted, in the presence of an alcohol, with 5-15 moles of paraformaldehyde and 3-10 moles of an ammonium salt.

The alcohol is preferably ethanol.

The ammonium salt may be selected from the group comprising ammonium acetate, ammonium chloride and combinations thereof.

In a variant of the process, reactants can be brought to the boil and reacted under reflux for a time shorter than or equal to 6 hours.

Finally, subject-matter of the invention is the use of 2,6-diphenyl-4,8-diazoadamantan-1-one and derivatives thereof as components for the formulation of solutions with sterilizing and disinfectant activity, in association with active principles with germicidal effect (like, e.g., peracetic acid, glutaraldehyde, ortho-phthalaldehyde, phenols, quaternary ammonium salts).

The main advantage of the chemical compounds according to the invention is to offer the option of having active principles at a lower concentration and reduced contact times to attain a microbicidal activity equal or superior to formulated products of the same type.

So far, a general description of the present invention has been provided; with the aid of the following examples, a more detailed description will hereinafter be provided of embodiments of the invention aimed at making better understood its objects, features, advantages and application modes.

In examples 3, 4 and 5 there may be used: as buffers, sodium and/or potassium phosphate or tetraborate; as anti-corrosion agents, benzotriazole or BHT (ButylHydroxyToluene) derivatives; as viscosity regulators, propylene glycol or glycerol; finally, as preservatives, methyl, ethyl and propyl derivatives of p-oxybenzoic acid may be used.

In examples 3, 4 and 5, identification of microbicidal features (sporicidal, mycobactericidal, virucidal, fungicidal, bactericidal effect) of the formulated products was entrusted to detections according to procedures validated in Europe and the USA.

The following procedures were adopted: EN 1040; EN 1276; EN 1650; EN 13624; EN 13727; EN 14348; EN 13697; EN 14347; EN 13704; EN 13610; EN 14476; EN 14937; AFNOR NF-T-72-231; AFNOR NF-T-72-190; Sporicidal Test n. 966.04 of Official Analytical Chemists (AOAC).

EXAMPLE 1

Characterization of 2,6-diphenyl-4,8-diazoadamantan-1-one

This molecule is soluble in propylene glycol and apolar organic solvents, whereas it is insoluble in water and ethanol.

Its raw formula is $C_{20}H_{20}ON_2$ and its molecular weight is 304.

Figure 1:
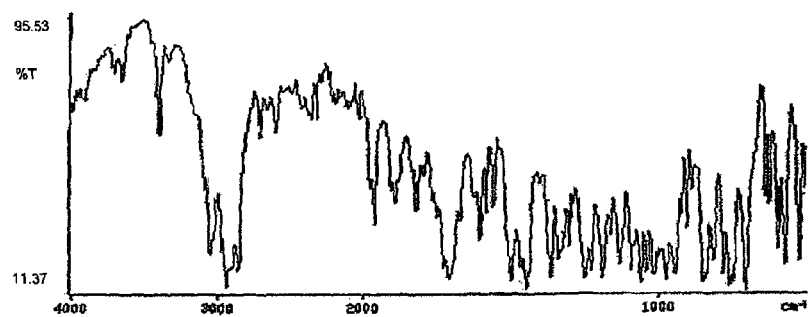
FIG. 1 shows the IR spectrum (infrared transmittance spectrum) of 2,6-diphenyl-4,8-diazoadamantan-1-one.

The IR spectrum shown in FIG. 1 was obtained by a Perkin Elmer apparatus, and the process adopted was that of: fluxing Nitrogen for about 30 min; performing an autotest; scanning (requirements: 8 $cm^{-1}$ resolution, strong apodization, 4400-450 $cm^{-1}$ range); printing the IR spectrum.

Figure 2:
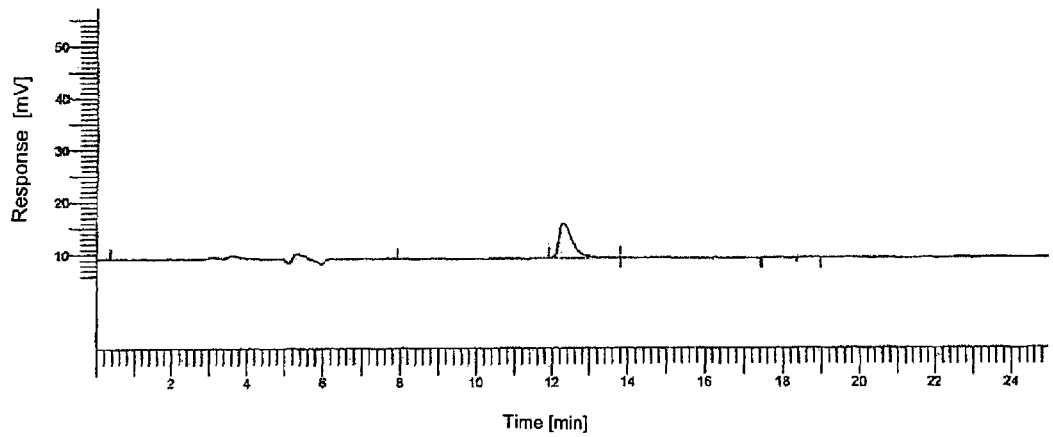
FIG. 2 shows the HPLC (High Performance Liquid Chromatography) chromatogram of 2,6-diphenyl-4,8-diazoadamantan-1-one.

The chromatogram of FIG. 2 for the assessment of molecular purity was obtained by a Perkin Elmer HPLC apparatus with detector and integrator. Chromatography was performed on SUPELCOSIL LC columns with precolumn under the following operative conditions:

wavelength: 245 nm
flow: 0.5 ml/min
temperature: room
mobile phase: eluent A/eluent B=66/34, where eluent A is acetonitrile for HPLC and eluent B is distilled water.

EXAMPLE 2

Manufacture of 2,6-diphenyl-4,8-diazoadamantan-1-one

Synthesis of the novel molecule was performed in a glass or stainless steel reactor having a convex bottom and provided with reflux condenser, heating jacket and adjustable-speed stirrer.

210 g dibenzylketone, 120 g formaldehyde and 230 g ammonium acetate were introduced in the reactor along with 500 ml 96° ethanol.

The mixture was heated to the boil.

Synthesis reaction was under reflux for a maximum time of 6 h and conducted under a hood. Prior to stopping the reaction, a sample of precipitate was collected and, after having washed it with ethanol, correspondence with an IR spectrum was checked.

When results were consistent, heating was stopped and precipitate cooled and collected; the latter was purified by washing (with ethanol) or solubilization and recrystallization.

EXAMPLE 3

Formulation of a First Series of Solutions with Sterilizing/Disinfectant Activity Solutions with sterilizing/disinfectant activity were prepared, with component concentration expressed as percent by weight, exhibiting compositions comprised in the following:

| | |
|---|---|
| 2,6-diphenyl-4,8-diazoadamantan-1-one | 0.050-0.150 |
| peracetic acid | 0.010-0.100 | the remainder consisting of coformulants (buffers, anticorrosion agents, viscosity regulators, preservatives) and water.

EXAMPLE 4

Manufacture of a Second Series of Solutions with Sterilizing/Disinfectant Activity Solutions with sterilizing/disinfectant activity were prepared, with component concentration expressed as percent by weight, exhibiting compositions comprised in the following:

| | |
|---|---|
| 2,6-diphenyl-4,8-diazoadamantan-1-one | 0.050-0.150 |
| peracetic acid | 0.150-0.250 |
| phenol derivative | 0.100-0.200 | the remainder consisting of coformulants (buffers, anticorrosion agents, viscosity regulators, preservatives) and water.

EXAMPLE 5

Manufacture of a Third Series of Solutions with Sterilizing/Disinfectant Activity Solutions with sterilizing/disinfectant activity were prepared, with component concentration expressed as percent by weight, exhibiting compositions comprised in the following:

| | |
|---|---|
| 2,6-diphenyl-4,8-diazoadamantan-1-one | 0.010-0.020 |
| peracetic acid | 0.050-0.150 |
| phenol derivative | 0.025-0.200 | the remainder consisting of coformulants (buffers, anticorrosion agents, viscosity regulators, preservatives) and water.

The invention claimed is:

1. A solution with sterilizing/disinfectant effect, comprising:
   0.050-0.150% by weight 2,6-diphenyl-4,8-diazoadamantan-1-one;
   0.150-0.250% by weight peracetic acid; and
   0.100-0.200% by weight of a phenol derivative,
   with the remainder comprising water and, optionally, at least one of a coformulant, a buffer, an anticorrosion agent, a viscosity regulator, or a preservative.

2. A solution with sterilizing/disinfectant effect, comprising:
   0.010-0.020% by weight 2,6-diphenyl-4,8-diazoadamantan-1-one;
   0.050-0.150% by weight peracetic acid; and
   0.025-0.200% by weight of a phenol derivative,
   with the remainder comprising water and, optionally, at least one of a coformulant, a buffer, an anticorrosion agent, a viscosity regulator, or a preservative.

* * * * *